United States Patent
Markman

(10) Patent No.: US 6,939,342 B2
(45) Date of Patent: Sep. 6, 2005

(54) SYSTEM AND METHOD FOR EVALUATING A SECONDARY LASIK TREATMENT

(75) Inventor: Howard P. Markman, Rochester, NY (US)

(73) Assignee: Bausch and Lomb Incorporated, Rochester, NY (US)

(*) Notice: Subject to any disclaimer, the term of this patent is extended or adjusted under 35 U.S.C. 154(b) by 0 days.

(21) Appl. No.: 10/318,443

(22) Filed: Dec. 12, 2002

(65) Prior Publication Data

US 2004/0116910 A1 Jun. 17, 2004

(51) Int. Cl.$^7$ .............................................. A61B 18/18
(52) U.S. Cl. ................................ 606/5; 606/4; 606/10; 128/898; 351/212
(58) Field of Search .......................... 606/4, 5, 10–12; 351/208–212; 128/898

(56) References Cited

U.S. PATENT DOCUMENTS

| | | | | |
|---|---|---|---|---|
| 5,777,719 A | * | 7/1998 | Williams et al. ............ 351/212 |
| 6,086,204 A | * | 7/2000 | Magnante ................... 351/212 |
| 6,129,722 A | * | 10/2000 | Ruiz ............................... 606/5 |
| 6,413,251 B1 | * | 7/2002 | Williams ........................ 606/5 |
| 6,569,154 B2 | * | 5/2003 | Campin et al. ................ 606/5 |
| 6,666,857 B2 | * | 12/2003 | Smith .......................... 606/12 |

FOREIGN PATENT DOCUMENTS

| WO | WO 01/28410 | 4/2001 | ........... A61B/3/107 |
|---|---|---|---|
| WO | WO 01/28477 | 4/2001 | ............. A61F/9/01 |
| WO | WO 02/07660 | 1/2002 | ............. A61F/9/01 |

* cited by examiner

Primary Examiner—A. Farah

(57) ABSTRACT

A method and system are disclosed for evaluating the safety of a prospective secondary LASIK treatment to correct a person's vision. The difficulties with making an accurate, direct measurement of corneal thickness of a cornea having a pre-existing keratectomy are overcome by using pre-LASIK topography and pachymetry measurements, and per- and post-LASIK wavefront measurements to determine post-LASIK corneal thickness, and thus the suitability and safety of a prospective secondary LASIK procedure. A system embodiment includes diagnostic and computing platforms for generating and analyzing data, and a device readable medium for storing and transferring an instruction to a laser ablation system.

13 Claims, 2 Drawing Sheets

SYSTEM AND METHOD FOR EVALUATING A SECONDARY LASIK TREATMENT

BACKGROUND OF THE INVENTION

1. Field of the Invention

The invention is generally directed to the field of vision correction by laser photoablation of corneal tissue, and more particularly, to a method and system for evaluating the safety of a prospective secondary LASIK treatment.

2. Description of Related Art

There are many approaches for correcting or improving a person's less than perfect vision. These include, for example, corrective spectacles, contact lenses, implanted lenses, and various forms of surgery on the eye. Over the past several years, tens of thousands of patients have undergone a type of refractive surgery known as laser in situ keratomileusis, commonly referred to as LASIK. In a typical LASIK procedure, the patient's vision defects are measured (typically limited to focussing and astigmatism errors), a hinged flap of corneal tissue is opened to expose a stromal layer of the cornea, and a laser beam is scanned over the exposed stromal tissue to ablate selected regions of the cornea. The corneal flap is then closed, and the cornea's new shape should provide the desired vision correction for the patient.

For a variety of reasons, an initial LASIK procedure does not always accomplish the desired vision correction goals in all patients. This can be due, for example, to eye movement during the surgery resulting in a decentered ablation, misalignment of the eye during surgery, inducement of secondary vision defects from the vision correction procedure itself, and for other reasons. It may be possible, however, to further correct the patient's vision with a secondary LASIK procedure. One of the primary considerations of a secondary LASIK procedure (and also the primary LASIK procedure) is whether the patient's cornea is thick enough to support the removal of tissue necessary to effect the corrective corneal profile. Based upon typical standards of care, the minimum residual corneal thickness of a person's eye should be greater than about 250 microns.

Corneal thickness is currently measured by measuring the anterior and posterior corneal position or corneal topography. This technique, however, is dependent on the ability to detect the edges or interfaces of corneal surfaces to determine their exact locations. While these techniques work well on a cornea that has not had refractive surgery such as LASIK, it is difficult to determine the position of the posterior corneal surface under the keratectomy, or LASIK flap, that is part of the LASIK procedure. The lack of precision in detecting the posterior corneal surface results in a poor estimate of post-LASIK corneal thickness. An accurate measurement of the corneal thickness remaining after a primary LASIK treatment is necessary to evaluate the safety of any secondary LASIK treatment and to determine the treatment plan.

The inventor has recognized the need for accurately measuring the post-LASIK corneal thickness of the patient's eye to evaluate the safety of a prospective secondary LASIK treatment. Accordingly, a system and method are presented below for making the necessary evaluation.

SUMMARY OF THE INVENTION

The invention is generally directed to a method and system for evaluating the safety of a secondary LASIK procedure to correct defective vision in a patient's eye.

An embodiment of the invention is directed to a method for evaluating the safety of a prospective secondary LASIK procedure. The method broadly includes the steps of obtaining a pre-LASIK corneal thickness measurement of the patient's eye, obtaining a pre-LASIK wavefront measurement of the patient's eye, determining an amount of corneal material removed by the primary LASIK procedure based upon the pre-LASIK corneal thickness and wavefront measurements of the patient's eye, and determining a post-LASIK corneal thickness as a difference between the pre-LASIK corneal thickness and the amount of tissue removed by the primary LASIK procedure. During the diagnostic process prior to a LASIK procedure, data would preferably be collected with topography equipment to measure the anterior corneal topography; topography or pachymetry equipment that would measure the posterior corneal position and with the anterior corneal topography provide corneal thickness data; and aberrometer equipment that would give the wavefront aberrations of the eye. The data could be stored in a patient file in the form of Zernike coefficients or any other form used to express a general surface. After the primary LASIK procedure, for some number of patients, a secondary treatment is needed to further improve vision. Prior to the secondary treatment, a wavefront measurement would be taken to determine the post-LASIK wavefront. The difference between the pre-LASIK wavefront and the post-LASIK wavefront is established. That difference, known as the optical path difference (OPD), when multiplied by a function of the corneal optical index (n−1) will give the amount of corneal material that was removed during the primary LASIK procedure. That difference, when subtracted from the pre-LASIK corneal thickness profile, will give an accurate measurement of the post-LASIK corneal thickness profile. The post-LASIK corneal thickness profile can be used to determine the safety of a secondary LASIK procedure.

In an aspect of this embodiment, a positive or a negative recommendation for further removal of corneal tissue can be indicated to the practitioner, for example, by displaying the recommendation on a graphical user interface (GUI), or by other indicators.

Another embodiment of the invention is directed to a system for determining the safety of a prospective secondary LASIK treatment. The system generally includes a diagnostic platform that is suitably equipped to obtain corneal thickness information about the patient's eye, and further suitably equipped to measure wavefront aberration error of the patient's eye. The system further includes a computing platform that can receive and store the diagnostic data and other data and determine a primary ablation profile for an initial (primary) LASIK treatment. The generated calculations will preferably indicate whether the patient's corneal thickness is sufficient to support the primary LASIK treatment. The computing platform will be capable of receiving and storing data diagnosing of a post-LASIK wavefront error of the patient's eye, and determining a secondary ablation profile that is indicative of an amount of corneal tissue to be removed by a prospective secondary LASIK treatment to create the desired visual outcome. The information supplied by the computing platform will further indicate whether the corneal thickness of the patient's eye is sufficient to support the secondary LASIK treatment.

An aspect of the system embodiment according to the invention further includes a device-readable medium which can store an executable instruction or a reference to an executable instruction for carrying out the prospective secondary LASIK treatment (and perhaps the primary LASIK treatment) by a laser system.

In a further aspect, a graphical user interface will be provided for displaying, among other things, information about whether it is safe to perform a secondary LASIK treatment on the patient's eye. Other information relevant to the LASIK procedure and optionally displayable on a graphical user interface may include, without limitation, refractive index information about the patient's eye, patient biographical data, clinician data, and system data.

DETAILED DESCRIPTION OF A PREFERRED EMBODIMENT OF THE INVENTION

Figure 1:
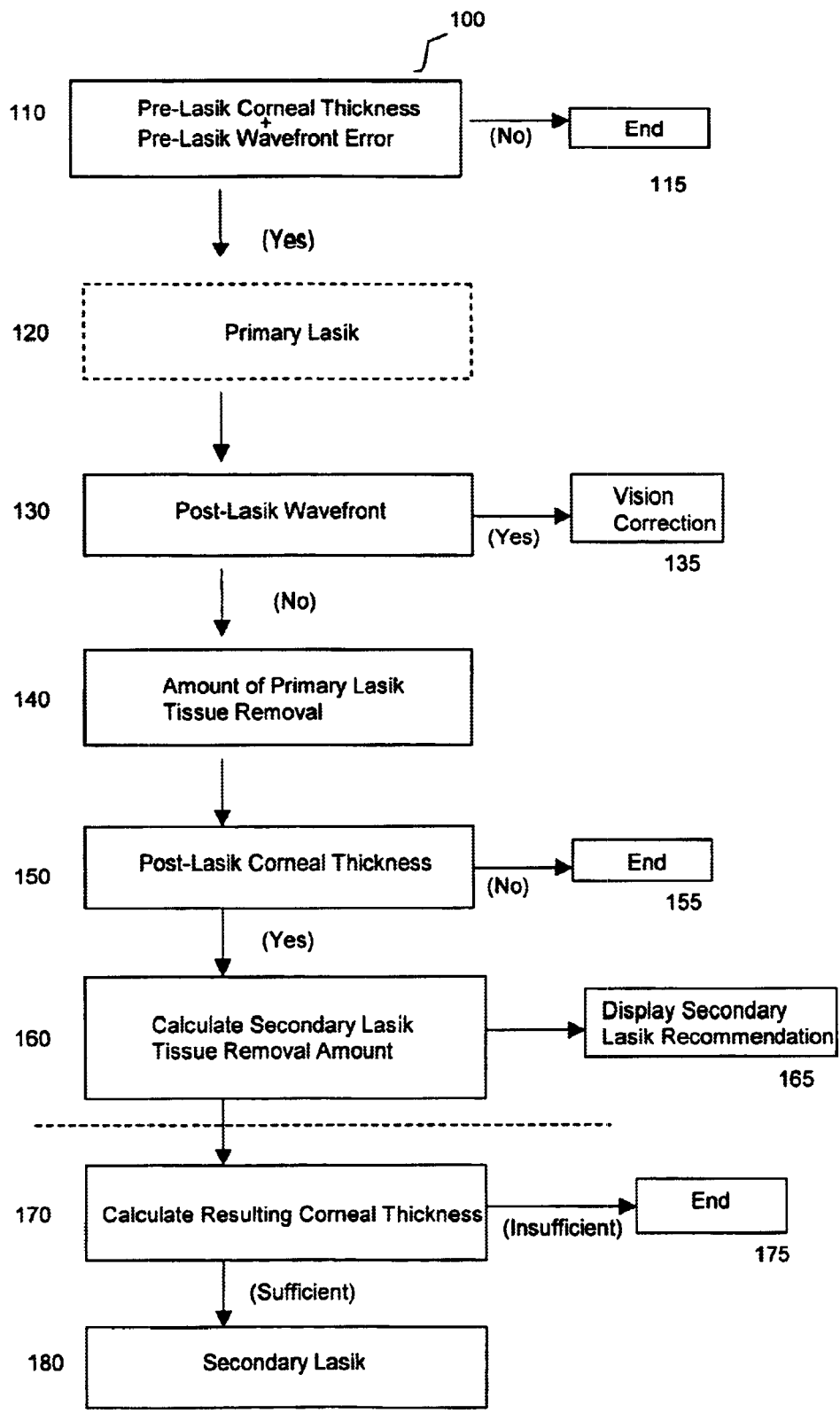
FIG. 1 is a flowchart setting forth a method according to an embodiment of the invention.

A method for evaluating the safety of a prospective secondary LASIK procedure is set forth in the blocked diagram in FIG. 1. The method 100 includes the steps of obtaining a pre-LASIK thickness measurement of the cornea and a pre-LASIK wavefront measurement of the patient's eye at block 110. The corneal thickness measurement data will preferably be obtained through topography and pachymetry measurement while the wavefront measurement is preferably obtained with the use of an aberrometer. Both of these types of devices are well-known in the art and are commercially available, therefore, they require no further description for an understanding of the instant invention. Assuming the pre-LASIK diagnostics do not contraindicate a primary LASIK procedure, which would then require alternative action as shown at 115, a primary LASIK procedure 120 is performed. It is to be noted that the primary LASIK procedure referred to herein is not in itself a part of the instant invention but is implicated as will be appreciated by a person skilled in the art in the consideration of a secondary LASIK procedure. After the primary LASIK procedure, further diagnostics are performed on the patient's eye to evaluate whether the desired vision correction was achieved. This is preferably done by a post-LASIK wavefront measurement as shown at 130. If the vision correction is satisfactory as shown at 135, then the invention described herein does not apply. However, as sometimes occurs, the primary ablative correction is misaligned or decentered and for these and/or other reasons the desired vision correction is not achieved, resulting in the potential for a corrective or secondary LASIK procedure. However, standards of care adhered to by most practitioners indicate a minimum corneal thickness that will support further corneal tissue removal. Typically, this is greater than about 250 microns. It is often extremely difficult if not impossible to measure the thickness of a post-LASIK cornea as those persons skilled in the art will appreciate. With knowledge of the corneal index of refraction in the pre- and post-LASIK wavefront information, the amount of corneal tissue removed by the primary LASIK procedure can be calculated as shown at 140. Simple subtraction then yields the post-LASIK corneal thickness as shown at 150. According to the invention, however, the post-LASIK wavefront measurement can be used to determine the extent of a further corrective procedure and by using the wavefront measurement in conjunction with the index of refraction of the eye, the amount of corneal tissue to be removed in a secondary LASIK procedure to obtain the desired vision correction can be easily calculated. If the post-LASIK corneal thickness is below a critical amount identified by the appropriate standard of care, then a secondary LASIK procedure will be contraindicated per se as shown at 155. However, if sufficient corneal thickness remains, the secondary wavefront measurement can be used to calculate a tissue removal algorithm for a secondary LASIK procedure as shown at block 160. Once again, simple subtraction will yield the prospective secondary post-LASIK corneal thickness as shown at 170. If this thickness is below the safe limit for a secondary procedure, then no secondary procedure will be performed as indicated at 175. Alternatively, if sufficient corneal thickness is present to support a secondary LASIK procedure, then the recommendation can be made for secondary LASIK procedure as shown at block 180.

Figure 2:
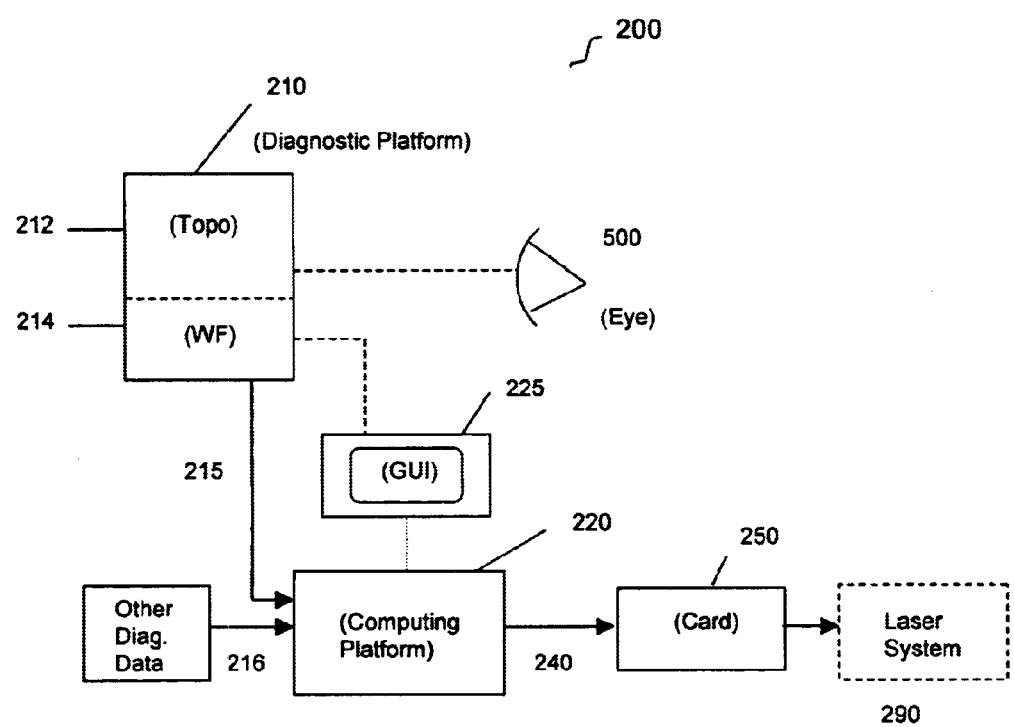
FIG. 2 is a diagrammatic illustration of a system according to an embodiment of the invention.

Another embodiment according to the invention relating to a system for determining the safety of a prospective secondary LASIK treatment is shown with reference to FIG. 2. The system 200 includes a diagnostic platform 210 for obtaining corneal thickness and wavefront aberration information about the patient's eye 500. Corneal thickness information is preferably obtained with a topography device 212 that measures anterior and posterior corneal topography and pachymetry. Other means are available for obtaining corneal thickness measurements including, but not limited to, optical coherence tomography (OCT) and ultrasound pachymetry, as known by those skilled in the art. An aberrometer 214 is the preferable device used to obtain pre- and post-LASIK wavefront measurements. Other devices known to those skilled in the art, for example, a refractometer may also be used to derive relevant wavefront information. The diagnostic platform 210 may comprise separate, connected components for obtaining the appropriate data or may comprise an integrated device capable of obtaining the necessary diagnostic information 215. Other information 216 may also be useful, and may include corneal index of refraction data, patient information, practitioner information, instrument information, and so on. The diagnostic platform 210 is operably connected to a computing platform 220 that can receive and store the diagnostic information 215 and the other information 216. The computing platform 220 will typically be suitable for determining a primary ablation profile indicative of an amount of corneal tissue to be removed by a primary LASIK treatment to effect a desired vision correction based upon the diagnostic and other data. A graphical user interface (GUI) 225 is operably connected to either the diagnostic platform 210 or the computing platform 220 and may indicate to the user whether the patient's eye is suited to the primary LASIK procedure. Assuming that a primary LASIK treatment is performed on the patient's eye, a post-LASIK wavefront measurement is performed on the patient's eye at some time thereafter as deemed appropriate by the practitioner to determine whether the desired vision correction has been achieved. As will be appreciated, the post-LASIK wavefront measurement need not be performed with the same diagnostic platform 210 used to obtain the pre-operative information; however, this scenario is shown for simplicity of description. In any event, if the desired vision correction was not achieved by the primary LASIK procedure, the post-LASIK wavefront information is input to the computing platform 220, and a secondary ablation profile is calculated that is determinative of an amount of corneal tissue that would be removed by a prospective secondary LASIK treatment to effect the desired vision correction. At this point, the practitioner will know whether the patient is a candidate for a secondary LASIK treatment. This information may be displayed in an appropriate form on the GUI 225. Assuming a secondary LASIK procedure is not contraindicated, the computing platform 220 can generate an instruction for carrying out a secondary LASIK procedure (and, of course, the primary LASIK procedure) which can be stored on an appropriate medium 250 such as a diskette, CD, DVD, memory card, or other appropriate medium that is commercially available for such purpose. The medium 250 can then be used in conjunction with a laser system 290 (not part of the invention per se) to effect the secondary LASIK treatment.

The foregoing description sets forth embodiments according to the invention for evaluating and/or determining the safety of performing a secondary LASIK treatment on a patient's eye to achieve a desired vision correction.

I claim:

1. A method for evaluating the safety of a prospective secondary LASIK procedure, comprising:
   a) obtaining a pre-LASIK corneal thickness measurement;
   b) obtaining a pre-LASIK wavefront measurement;
   c) obtaining a post-LASIK wavefront measurement;
   d) determining an amount of corneal material removed by the LASIK procedure from (b) and (c); and
   e) determining the post-LASIK corneal thickness from the difference between (a) and (d), thereby determining the safety of the procedure.

2. The method of claim 1, wherein step (a) comprises obtaining an anterior corneal topography measurement, a posterior corneal topography measurement, and a corneal pachymetry measurement.

3. The method of claim 1, wherein step (d) comprises determining the optical path difference between the pre- and post-LASIK wavefront measurements and using this information with index of refraction data to determine the removed tissue amount.

4. The method of claim 1, further comprising
   using the post-LASIK wavefront measurement to determine an amount of a prospective secondary corneal tissue removal for a desired vision correction; and
   determining whether the post-LASIK corneal thickness is sufficient to support a recommendation for the secondary corneal tissue removal.

5. The method of claim 4, further comprising indicating one of a positive and a negative recommendation for the further removal of corneal tissue.

6. The method of claim 4, comprising displaying the recommendation on a graphical user interface.

7. A system for determining the safety of a prospective secondary LASIK treatment, comprising:
   a diagnostic platform including a component adapted to measure data indicative of a corneal thickness of a patient's eye, and a component adapted to measure data indicative of a wavefront error of the patient's eye, prior to a LASIK treatment on the eye;
   a computing platform operatively connected to the diagnostic platform, capable of receiving and storing the diagnostic data and other data, and determining a primary ablation profile that is indicative of an amount of corneal tissue to be removed by a primary LASIK treatment to effect a desired vision correction based upon the diagnostic and other data, wherein the computing platform will provide an indicia of whether the corneal thickness is sufficient for the primary LASIK treatment based upon a primary corneal thickness measurement;
   wherein the computing platform is capable of receiving and storing data indicative of a post-LASIK wavefront error of the patient's eye and determining a secondary ablation profile that is indicative of an amount of corneal tissue to be removed by a prospective secondary LASIK treatment to effect the desired vision correction, further wherein the computing platform is programmed to determine the difference between the primary corneal thickness measurement and the amount of corneal tissue removed by the primary LASIK procedure.

8. The system of claim 7 further comprising a device readable medium operably compatible with the computing platform and adapted to receive an instruction reference relating to at least one of the primary ablation profile and the secondary ablation profile, said medium being further operably compatible with a laser system for effecting said primary or secondary LASIK procedure.

9. The system of claim 7 further comprising a graphical user interface (GUI) operably connected to one of the diagnostic platform and the computing platform.

10. The system of claim 9, wherein the GUI can display a recommendation for the secondary LASIK treatment.

11. The system of claim 7, wherein the component adapted to measure data indicative of a corneal thickness of a patient's eye includes at least one of a topography device, an OCT device, and an ultrasonic pachymetry device; and the component adapted to measure data indicative of a wavefront error of the patient's eye includes at least one of an aberrometer, an interferometer, and a refractometer.

12. The system of claim 7, wherein the other data comprises at least one of index of refraction data, patient data, clinician data, and system data.

13. The system of claim 7, wherein the diagnostic platform is an integrated device adapted to provide the necessary diagnostic data to the computing platform.

* * * * *